United States Patent

Abushanab et al.

[11] Patent Number: 5,994,559
[45] Date of Patent: Nov. 30, 1999

[54] SYNTHESIS OF MONATIN-A HIGH INTENSITY NATURAL SWEETENER

[75] Inventors: Elie Abushanab, Peace Dale; Subramaniam Arumugam, Exeter, both of R.I.

[73] Assignee: The Board of Governors for Higher Education, State of Rhode Island and Providence Plantations, Providence, R.I.

[21] Appl. No.: 09/131,085

[22] Filed: Aug. 6, 1998

[51] Int. Cl.$^6$ ................................... C07D 209/18
[52] U.S. Cl. ............................................. 548/495
[58] Field of Search ............................. 548/495

[56] References Cited

U.S. PATENT DOCUMENTS 4,975,298  12/1990  Van Wyk et al. .
5,128,164  7/1992  Van Wyk et al. .
5,128,482  7/1992  Olivier et al. .

FOREIGN PATENT DOCUMENTS 0 438 314 A1  7/1991  European Pat. Off. .

OTHER PUBLICATIONS

Holzapfel, et al., A simple cycloaddition approach to a racemate of the natural sweetener monatin, Synthetic Communications, 24(22), 3197–3211 (1994).

Vleggaar, et al., Structure elucidation of monatin, a high-intensity sweetner isolated from the plant *Schlerochiton ilicifolius,* J. Chem. Soc. Perkin Trans., 3095–3098, (1992).

*Primary Examiner*—Joseph K. McKane
*Assistant Examiner*—John F. Dolan
*Attorney, Agent, or Firm*—Samuels, Gauthier & Stevens

[57] ABSTRACT

The high intensity natural sweetener monatin, an α-amino acid (1) is synthesized from readily available starting materials. Regiospecific ring opening of epoxide (9) with indole magnesium bromide yields lactone (11). Amination of (11) followed by saponification yields Monatin.

1 Claim, No Drawings

SYNTHESIS OF MONATIN-A HIGH INTENSITY NATURAL SWEETENER

BACKGROUND OF THE INVENTION

1. Field of the Invention

The invention relates to the synthesis of monatin.

2. Description of the Prior Art

The undesirable effects associated with the high consumption of sugar such as obesity and tooth decay have resulted in an intensive search for natural and synthetic substitutes. Although a number of non-nutritive sweeteners have been approved for public consumption, such as saccharin, cyclamate, acesulfame-K and aspartame, none fulfill the requirements of being safe, non-caloric, stable over a wide range of pHs and temperatures with a long shelf-life, and no aftertaste. The concern about long term effects of some of these products has resulted in the search for high intensity sweeteners from natural sources.

There are a number of naturally occurring compounds such as stevioside and glycyrrhizin that are used as sweeteners in Europe and Japan but none have been approved for use as such in the United States. Monatin is a high intensity, low-caloric sweetener that was isolated from the bark of the roots of *Schlerochiton ilicifolius*, found in the northern Transvaal region of South Africa. Its relative sweetness was determined to be 1400 times that of sucrose. It was found to create highly acceptable blend with other sweeteners such as aspartame in a variety of flavors with or without carbonation. The limited amounts in the dried bark (0.007%) has spurred efforts to develop synthetic methodologies to produce ample supplies of the sweetener and to prepare analogs to assess the relationship between structure and sweetness.

Structural and stereochemical analyses of monatin established it to be (2S,4S) 2-amino-4-carboxy-4-hydroxy-5-(3-indolyl)pentanoic acid 1. There are two reported syntheses of monatin that are retrosynthetically outlined in Scheme 1. the first deals with the preparation of a key keto ester 2 from indole acetic acid and an activated L-aspartate, Holzapfel, C. W.; Olivier, *Synth. Commun.*, 1993, 23, 2511. The second is based upon a 2+3 cycloaddition reaction between indolyl acrylate 6 and formonitrile oxide 7 to form isoxazoline 5 from which monatin is obtained, Holzapfel, C. W.; Bischofberger, K.; Olivier, *Synth. Commun.*, 1994, 38, 7025. Both are multistep routes and suffer from low yields in certain steps.

SUMMARY OF THE INVENTION

Broadly the invention comprises an economic, versatile and scalable synthesis of monatin that is adaptable for the preparation of chiral isomers and new analogs for taste evaluations.

Referring to Scheme I, retrosynthetic analyses of 1 to indole, whose regiospecific condensation with an epoxy ester 9 generated the required substitution at C3.

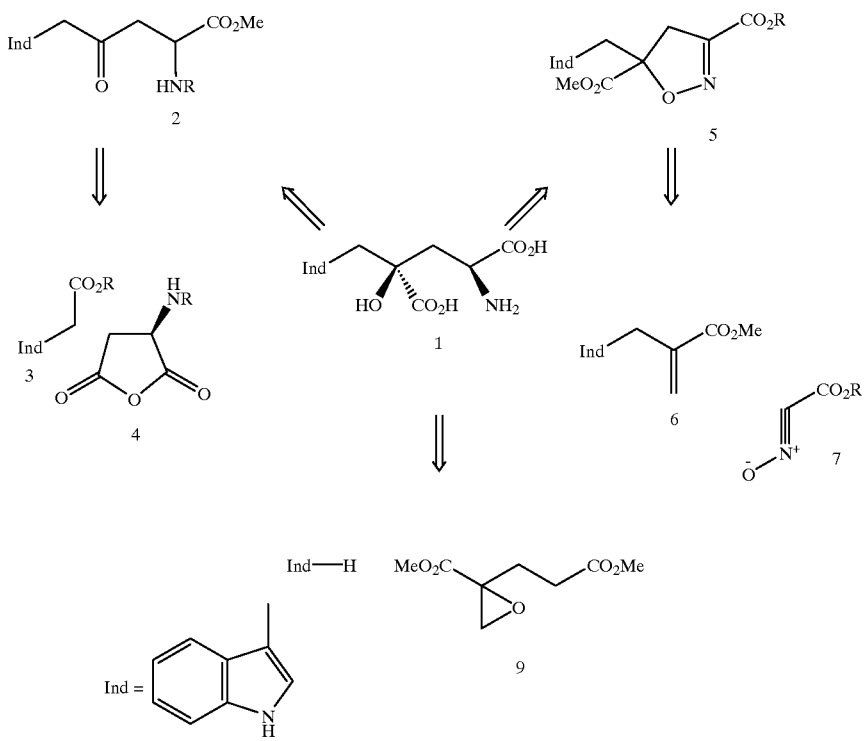

The synthetic pathway to monatin 1 is outlined in Scheme 2.

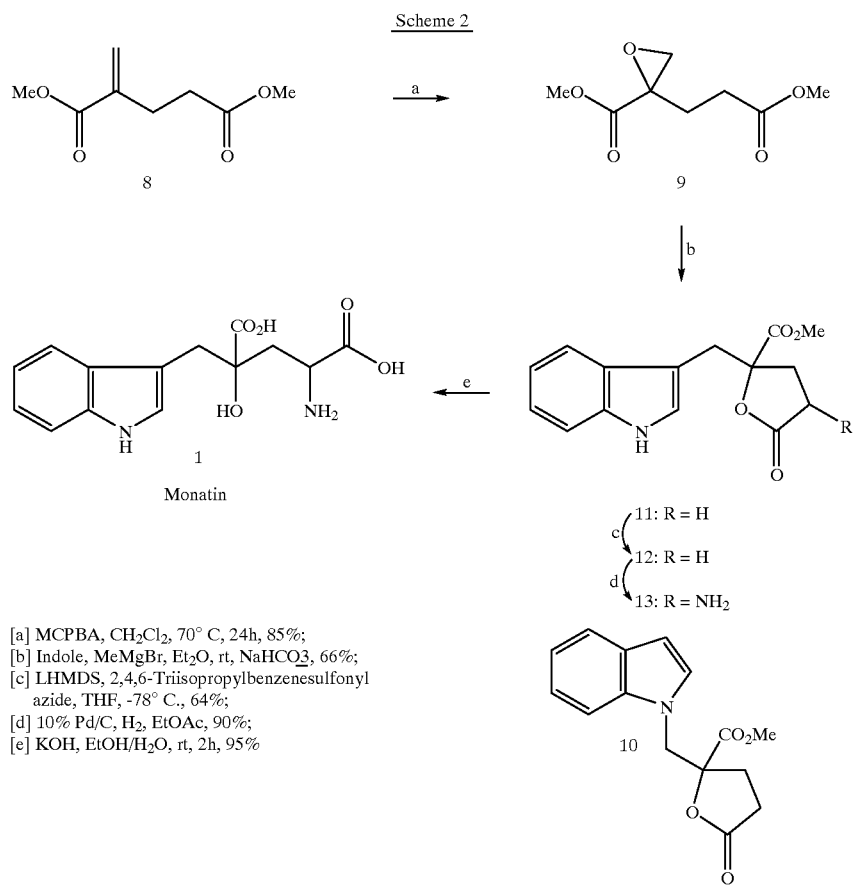

[a] MCPBA, CH$_2$Cl$_2$, 70° C, 24h, 85%;
[b] Indole, MeMgBr, Et$_2$O, rt, NaHCO$_3$, 66%;
[c] LHMDS, 2,4,6-Triisopropylbenzenesulfonyl azide, THF, -78° C., 64%;
[d] 10% Pd/C, H$_2$, EtOAc, 90%;
[e] KOH, EtOH/H$_2$O, rt, 2h, 95%

Dimethyl-2-methylene glutarate 8 was obtained by BU$_3$P catalyzed dimerization of methyl acrylate, Rauhut, M. M.; Carrier, H., U.S. Pat. No. 3,074,999, 1963; and Nagato, N.; Ogawa, M.; Naito, T., Japan Kokai 7386816, 1973. Oxidation of 8, with m-chloroperbenzoic acid furnished epoxide 9 in 85% isolated yield.

Regiospecific ring opening of epoxide 9, Ghosh, A.; Wang, W.; Freeman, J. P.; Althas, J. S.; Von Voigtlander, P. F.; Scahill, T. A.; Mizsak, S. A.; Szmuszkovicz, J., *Tetrahedron*, 1991, 47, 8653, with indole magnesium bromide followed by in situ base catalyzed lactonization with NaHCO$_3$ furnished two products in 12 and 66% yield whose structures were assigned based on $^1$H NMR analysis, The minor 10 was the result of N-alkylation having no NH signal and a proton doublet at C3 (δ 6.58). The major product proved to be the desired lactone 11 with an exchangeable indole proton at δ 9.25 and an AB quartet at 3.38 ppm for the methylene protons at C3.

The α-deprotonation of lactone 11 with lithium hexamethyldisilazide followed by azide transfer from the hindered electrophile 2,4,6-triisopropylbenzenesulfonyl azide, Evans, D. A.; Evrad, D. A.; Rychnovsky, S. D.; Fruh, T.; Whittingham, W. G.; DeVries, K. M., *Tetrahedron Lett.*, 1992, 33, 1189, (trisyl azide; prepared in quantitative yield from trisyl chloride) afforded azido lactone 12 as a 3:2 diastereomeric mixture. The most distinctive $^1$H NMR feature of 12 is the difference in the chemical shifts of the azido protons (δ 3.36 & 4.40 ppm), both appearing as doublet of doublets. It is presumed that the more deshielded proton has cis stereochemistry to the methoxycarbonyl group.

Catalytic hydrogenation of azido lactone 12 gave amino lactone 13 in nearly quantitative yield as a 3:2 diastereomeric mixture. Base catalyzed hydrolysis of amino lactone 13 gave racemic monatin 1.

It is evident from this synthesis that chiral isomers of monatin can be obtained following the same route described in Scheme 2, by using an optically active epoxide 9. This can be obtained by AD-mix oxidation of olefin 8, Cha, J. K.; Kim, N. S., *Chem Rev.*, 1995, 95, 1761; and Kolb, H. C.; VanNiewwenhz, M. S.; Sharpless, K. B., *Chem Rev.*, 1994, 94, 2483, followed by Mitsunobu dehydration of the resultant diol, Abushanab, E.; Vemishetti, P.; Leiby, R. W.; Singh, H. K.; Mikkilineni, A. B.; Wu, D. C. J.; Saibaba, R.; Panzica, R. P., *J. Org. Chem.*, 1988, 53, 2598. The newly created chiral center can induce asymmetry in the conversion of 11 to 12 leading to optically pure monatin isomers.

DESCRIPTION OF THE PREFERRED EMBODIMENT

Experimental

General

All reactions were run in oven-dried glassware, sealed with a rubber septum, and stirred with a magnetic stirring bar under N$_2$. Unless otherwise noted, materials were obtained from commercial suppliers and were used without purification. Ether was dried with $LiAlH_4$ and distilled under nitrogen. THF was distilled from sodium benzophenone ketyl just prior to use. Flash chromatography was performed on Fisher Scientific silica gel 230–400 mesh. Melting points are reported uncorrected.

Methyl 4,5-epoxy-4-methoxycarbonylpentanoate (9)

To an ice cold solution of the olefin 8 (3.44 g, 20 mmol) in $CH_2Cl_2$ (100 mL) was added 55% m-chloroperbenzoic acid (7.54 g, 24 mmol). After stirring the reaction mixture at room temperature for 24 h, it was diluted with ethyl actate (300 mL), washed successively with saturated $NaHCO_3$ (150 mL), 10% $NaHSO_3$ (150 mL), saturated $NaHCO_3$ (150 mL), and brine, and dried ($MgSO_4$). The residue obtained after evaporation of ethyl acetate was purified by distillation to afford pure epoxide 9 (3.20 g, 85%); bp. 110–112° C./4 mm; $^1H$ NMR (300 MHz, $CDCl_3$ (δ 2.01–2.10 (m, 1H), 2.38–2.54 (m, 3H), 2.84 (d, 1H, J=5.8 Hz), 3.10 (d, 1H, J=5.8 Hz), 3.67 (s, H), 3.77 (s, H); $^{13}C$ NMR (75 MHz, $CDCl_3$) δ 26.55, 29.42, 51.72, 51.99, 52.62, 55.89, 170.36, 1792.96. Anal. Calcd for $C_8H_{12}O_5$: C, 51.06; H, 6.38. Found C, 51.03; H, 6.46.

4-(3-Indolylmethyl)-4-methoxycarbonyl-γ-butyrolactone (11)

To a well-stirred solution of indole (2.90 g, 24.8 mmol) in $Et_2O$ (10 mL) under nitrogen was added dropwise a solution of methyl magnesium bromide (3.0 M, 8.3 mL, 25 mmol) at room temperature. The rate of addition was adjusted to maintain a gentle reflux. After completion of the addition, the resulting solution was stirred another 45 min at room temperature. A solution of epoxide 9 (4.70 g, 25 mml) in $Et_2O$ (10 mL) was then added dropwise, followed by 20 mL of $Et_2O$ and left stirring overnight (12 h). The reaction was quenched slowly by the dropwise addition of a saturated solution of $NaHCO_3$ (30 mL), filtered and the white precipitate was washed repeatedly with EtOAc (4×50 mL). The combined organic layer was dried and evaporated under reduced pressure to leave a brown residue. This was purified by silica gel column chromatography eluting with EtOAc-hexanes (2:8) to afford pure 10 (0.80 g, 12%). A sample was crystallized from ethyl acetate/hexanes: mp. 100–102° C.; $^1H$ NMR (90 MHz, $CDCl_3$) δ 2.22–2.44 (m, 2H), 2.72–3.40 (m, 2H), 3.62 (ABq, 2H, J=10.2 Hz), 3.81 (s, 3H), 6.58 (d, 1H, J=3.3 Hz), 7.16–7.74 (m, 4H), 8.36 (d, 1H J=8.4 Hz). Anal. Calcd for $C_{15}H_{15}NO_4$: C, 65.93; H, 5.50; N, 5.13. Found: C, 65.89; H, 5.46; N, 5.12. Further elution with EtOAc-hexanes (3:7) gave pure indole lactone 11 (4.42 g, 66%). Analytical sample was crystallized from acetonitrile to afford a white solid: mp. 168–170° C., $^1H$ NMR (300 MHz, $CD_3CN$) δ 2.19–2.49 (m, 4H), 3.38 (ABq, 2H, J=15.1 Hz), 3.69 (s, H), 7.04–7.16 (m, 3H), 7.40 (d, 1H, J=8.0 Hz), 7.59 (d, 1H, J=7.6 Hz); 9.25 (brs, 1H, $D_2O$ Exchangeable); $^{13}C$ NMR (75 MHz, $CD_3CN$) δ 28.97, 31.40, 33.60, 53.41, 88.34, 109.28, 112.47, 120.03, 120.29, 122.75, 125.85, 129.13, 137.38, 173.23, 177.13. Anal. Calcd for $C_{15}H_{15}NO_4$; C, 65.93; H, 5.50; N, 5.13. Found: C, 66.10; H, 5.49; N, 5.22.

2-Azido-4-(3-indolylmethyl)-4-methoxycarbonyl-γ-butyrolactone (12)

To a solution of LHMDS (1.0 M, 24.2 mL, 24.2 mmol) in THF was added indole lactone 11 (3.00 g, 11 mmol) in freshly distilled THF (33 mL) at −78° C. The light yellow solution was stirred for 40 min, and triisopropylbenzenesulfonyl azide (3.40 g, 11 mmol) in 33 mL dry THF was added at −78° C. via syringe. The reaction mixture was stirred for 20 min before quenching with acetic acid (49.5 mmol, 2.83 mL). The reaction mixture was allowed to warm to room temperature over 30 min before being diluted with saturated $NH_4Cl$ solution. This solution was stirred for 5 min and extracted with EtOAc (2×75 mL). The combined organic layers were dried ($MgSO_4$), and the solvent was removed under reduced pressure. The crude oil was flash chromatographed on silica gel (1:2, EtOAc-hexanes eluant) to afford 2.21 g (64%) of pure azido lactone 12 as a mixture of diastereomers (3:2; SS/RR:SR/RS). A sample was crystallized from ethyl acetate/hexanes: mp. 110–112° C., SS/RR recemate; $^1H$ NMR (300 MHz, $CDCl_3$) δ 2.19 (dd, 1H, J=14.0, 7.3 Hz), 2.63 (dd, 1H, J=14.0, 9.3 Hz), 3.34 (dd, 1H, J=9.0, 2.6 Hz), 3.39 (ABq, 2H, J=15.3 Hz), 3.84 (s, 3H), 7.10 (d, J=2.4 Hz), 7.14–7.24 ((m, 2H), 7.37 (d, 1H, J=8.3 Hz), 7.63 (d, 1H, J=7.6 Hz), 8.32 (brs 1H, $D_2O$ Exchangeable).

$^{13}C$ NMR (75 MHz, $CDCl_3$) δ 32.57, 35.82, 53.24, 56.84, 85.16, 106.97, 111.64, 118.36, 120.37, 122.67, 125.04, 127.47, 135.99, 171.12, 172.14. SR/RS recemate: $^1H$ NMR (300 MHz, $CDCl_3$) δ 2.13 (dd, 1H, J=13.4, 110 Hz), 2.79 (dd, 1H, J=13.4, 8.9 Hz), 3.45 ($Ab_q$, 2H, J=15.3 Hz), 3.74 (s, 3H), 4.40 (dd, 1H, J=10.9, 9.0 Hz), 7.13 (d, 1H, J=2.3 Hz) 7.14–7.24 (m, 2H), 7.40 (d, 1H, J=8.0 Hz), 7.58 (d, 1H, J=7.5 Hz), 8.23 (brs, 1H, $D_2O$ Exchangeable). Anal. Calcd for $C_{15}H_{14}N_4O_4$: C, 57.33; H, 4.46; N, 17.8. Found: C, 57.15; H, 462; N, 17.78.

2-Amino-4-(3-inodolylmethyl)-4-methoxycarbonyl-γ-butyrolactone (13)

To a solution of the azide 12 (0.63 g, 2.0 mmol) in EtOAc (30 mL) was added 10% Pd/C (0.12 g). The flask was charged with $H_2$ (1 atm) and the solution was stirred at room temperature. After 2 h the catalyst was filtered off and the solvent was removed in vacuo. Purification of the residue by flash chromatography using EtOAc as eluent gave amino lactone 13 (0.52 g, 90%) as a mixture of diastereomers (3:2; SS/RR:SR/RS). A sample was crystallized from ethyl acetate/hexanes to afford a white soild: mp. 188–189° C.; SS/RR racemate: $^1H$ NMR (500 MHz, $CD_3CN$) δ 1.54 (brs, 2H $D_2O$ Exchangeable), 2.16 (dd, 1H, J=13.2, 9.3 Hz), 2.71 (dd, 1H, J=13.2, 9.2 Hz), 3.34 ($AB_q$, 2H, J=15.0 Hz), 3.66 (s, 3H), 3.67–3.70 (m, 1H), 7.05–7.15 (m, 2H), 7.39 (d, 1H, J=7.9 Hz), 7.56 (d, 1H, J=8.0 HZ), 9.24 (brs, 1H, $D_2O$ Exchangeable). SR/RS racemate: δ 1.54 (brs. 2H, $D_2O$ Exchangeable), 2.06 (t, 1H, J=12.3 Hz), 2.79 (dd, 1H, J=12.9, 9.6 Hz), 3.17 (t, 1H, J=9.2 Hz), 3.38 (ABq, 2H, J=15.1 Hz), 3.71 (s, 3H), 7.05–7.15 (m, 2H), 7.40 (d, 1H, J=8.0 Hz), 7.59 (d, 1H, J=7.9 Hz), 9.28 (brs, 1H, $D_2O$ Exchangeable). Anal. Calcd for $C_{15}H_{16}N_2O_4$: C, 62.50; H, 5.56; N, 9.72. Found: C, 62.35; H, 5.38; N, 9.62.

2-Amino-4-carboxy-4-hydroxy-5-(3-indolyl)pentanoicacid

A solution of amino ester 13 (0.25 g, 0.87 mmol) and potassium hydroxide (0.11 g, 1.96 mmol) in 5 mL 80% ethanol was stirred for 2 h at room temperature. This solution was passed through an ion-exchange resin (Biorad, AG 50W-X8, 3 mL) and the resin was rinsed with a 15 mL 80% ethanol solution. Removal of the solvent in vacuo afforded a pale yellow crystalline product monatin 1 (0.24 g, 95%) as racemates. SS/RR racemate: $^1H$ NMR (300 MHz, $D_2O$) δ 1.90 (dd, 1H, J=13.5, 8.7 Hz), 2.23–2.38 (m, 1H), 3.11 ($AB_1$, 2H, J=14.6 Hz), 3.10–3.17 (m, 1H), 7.12–7.22 (m, 2H), 7.24 (s, 1H), 7.46–7.49 (m, 1H), 7.70 (d, 1H J=7.7 Hz). SR/RS racemate: $^1H$ NMR (300 MHz, $D_2O$) δ 2.26–2.39 (m, 1H), 2.79 (dd, 1H, J=13.2, 7.4 Hz), 3.19 ($AB_q$, 2H, J=13.5 Hz), 4.11 (dd, 1H, J=9.1, 5.0 Hz), 7.12–7.22 (m, 2H), 7.30 (s, 1H), 7.46–7.49 (m, 1H), 7.72 (d, 1H, J=7.8 Hz).

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A method for the synthesis of

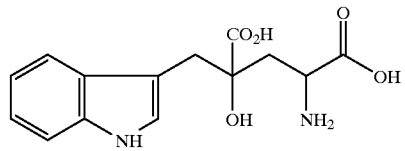
(1)

which comprises:

opening the ring of the active epoxy ester

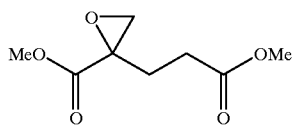
(9)

by reacting with indole magnesium bromide followed by in situ base catalyzed lactonization to produce

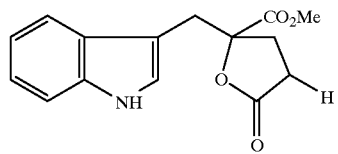
(11)

effecting α-deprotonation of lactone (11) with lithium hexamethyldisilazide followed by azide transfer from the hindered electrophile 2,4,6-triisopropylbenzenesulfonyl azide to produce

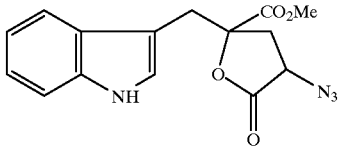
(12)

catalytically hydrogenating (12) to produce

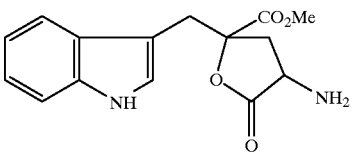
(13)

and effecting base catalyzed hydrolysis of (13) to produce (1).

* * * * *